United States Patent
Medvedev et al.

(10) Patent No.: US 10,856,748 B2
(45) Date of Patent: Dec. 8, 2020

(54) HEART BEAT IDENTIFICATION AND PUMP SPEED SYNCHRONIZATION

(71) Applicant: TC1 LLC, Pleasanton, CA (US)

(72) Inventors: Alexander Medvedev, Ann Arbor, MI (US); Shunzhou Yu, Ann Arbor, MI (US); Ren You, Windsor (CA)

(73) Assignee: TC1 LLC, Pleasanton, CA (US)

( * ) Notice: Subject to any disclaimer, the term of this patent is extended or adjusted under 35 U.S.C. 154(b) by 0 days.

(21) Appl. No.: 16/714,287

(22) Filed: Dec. 13, 2019

(65) Prior Publication Data

US 2020/0187787 A1 Jun. 18, 2020

Related U.S. Application Data

(63) Continuation of application No. 16/050,889, filed on Jul. 31, 2018, now Pat. No. 10,506,935, which is a continuation of application No. 15/041,716, filed on Feb. 11, 2016, now Pat. No. 10,052,420.

(60) Provisional application No. 62/114,886, filed on Feb. 11, 2015.

(51) Int. Cl.
| | | |
|---|---|---|
| *A61M 1/10* | (2006.01) | |
| *A61B 5/024* | (2006.01) | |
| *A61M 1/00* | (2006.01) | |
| *A61M 1/12* | (2006.01) | |

(52) U.S. Cl.
CPC .......... *A61B 5/024* (2013.01); *A61B 5/02438* (2013.01); *A61M 1/00* (2013.01); *A61M 1/1046* (2013.01); *A61M 1/1086* (2013.01); *A61M 1/101* (2013.01); *A61M 1/1005* (2014.02);
(Continued)

(58) Field of Classification Search
CPC .. A61M 1/1086; A61M 1/1046; A61M 1/101; A61M 1/1005; A61M 1/122
See application file for complete search history.

(56) References Cited

U.S. PATENT DOCUMENTS

| | | |
|---|---|---|
| 1,093,868 A | 4/1914 | Leighty |
| 2,684,035 A | 7/1954 | Kemp |
| 3,023,334 A | 2/1962 | Burr et al. |
(Continued)

FOREIGN PATENT DOCUMENTS

| | | | |
|---|---|---|---|
| CN | 1347585 A | 5/2002 | |
| CN | 1462344 A | 12/2003 | |
(Continued)

OTHER PUBLICATIONS

Extended European Search report dated Apr. 2, 2013, in European Patent Application No. 10748702.7, all pages.
(Continued)

*Primary Examiner* — Rex R Holmes
(74) *Attorney, Agent, or Firm* — Kilpatrick Townsend & Stockton LLP

(57) ABSTRACT

A method for synchronizing operation of a heart assist pump device to a patient's cardiac cycle includes obtaining a signal from a motor of a heart assist pump device and filtering the signal to remove noise. The method also includes determining a speed synchronization start point at which time the motor of the heart assist pump device will begin a change in speed of operation based on the filtered signal. The method further includes modulating a speed of the motor of the heart assist pump device to a target speed at the speed synchronization start point, thereby synchronizing the change in speed of operation with a patient's cardiac cycle.

20 Claims, 8 Drawing Sheets

(52) U.S. Cl.
CPC ..... *A61M 1/122* (2014.02); *A61M 2205/3334* (2013.01); *A61M 2230/04* (2013.01)

(56) References Cited

U.S. PATENT DOCUMENTS

| | | |
|---|---|---|
| 3,510,229 A | 5/1970 | Smith |
| 3,620,638 A | 11/1971 | Kaye et al. |
| 3,870,382 A | 3/1975 | Reinhoudt |
| 3,932,069 A | 1/1976 | Giardini et al. |
| 3,960,468 A | 6/1976 | Boorse et al. |
| 4,149,535 A | 4/1979 | Voider |
| 4,382,199 A | 5/1983 | Isaacson |
| 4,392,836 A | 6/1983 | Sugawara |
| 4,434,389 A | 2/1984 | Langley et al. |
| 4,507,048 A | 3/1985 | Belenger et al. |
| 4,528,485 A | 7/1985 | Boyd, Jr. |
| 4,540,402 A | 9/1985 | Aigner |
| 4,549,860 A | 10/1985 | Yakich |
| 4,645,961 A | 2/1987 | Maisky |
| 4,686,982 A | 8/1987 | Nash |
| 4,688,998 A | 8/1987 | Olsen et al. |
| 4,753,221 A | 6/1988 | Kensey et al. |
| 4,769,006 A | 9/1988 | Papatonakos |
| 4,779,614 A | 10/1988 | Moise |
| 4,790,843 A | 12/1988 | Carpentier et al. |
| 4,806,080 A | 2/1989 | Mizobuchi et al. |
| 4,817,586 A | 4/1989 | Wampler |
| 4,846,152 A | 7/1989 | Wampler et al. |
| 4,857,781 A | 8/1989 | Shih |
| 4,888,011 A | 12/1989 | Kung et al. |
| 4,895,557 A | 1/1990 | Moise et al. |
| 4,900,227 A | 2/1990 | Troup lin |
| 4,902,272 A | 2/1990 | Milder et al. |
| 4,906,229 A | 3/1990 | Wampler |
| 4,908,012 A | 3/1990 | Moise et al. |
| 4,919,647 A | 4/1990 | Nash |
| 4,930,997 A | 6/1990 | Bennett |
| 4,944,722 A | 7/1990 | Carriker et al. |
| 4,957,504 A | 9/1990 | Chardack |
| 4,964,864 A | 10/1990 | Summers et al. |
| 4,969,865 A | 11/1990 | Hwang et al. |
| 4,985,014 A | 1/1991 | Orejola |
| 4,995,857 A | 2/1991 | Arnold |
| 5,021,048 A | 6/1991 | Buckholtz |
| 5,078,741 A | 1/1992 | Bramm et al. |
| 5,092,844 A | 3/1992 | Schwartz et al. |
| 5,092,879 A | 3/1992 | Jarvik |
| 5,100,374 A | 3/1992 | Kageyama |
| 5,106,263 A | 4/1992 | Irie |
| 5,106,273 A | 4/1992 | Lemarquand et al. |
| 5,106,372 A | 4/1992 | Ranford |
| 5,112,202 A | 5/1992 | Ozaki et al. |
| 5,129,883 A | 7/1992 | Black |
| 5,145,333 A | 9/1992 | Smith |
| 5,147,186 A | 9/1992 | Buckholtz |
| 5,112,349 A | 12/1992 | Summers et al. |
| 5,190,528 A | 2/1993 | Fonger et al. |
| 5,201,679 A | 4/1993 | Velte et al. |
| 5,211,546 A | 5/1993 | Isaacson et al. |
| 5,229,693 A | 7/1993 | Futami et al. |
| 5,275,580 A | 1/1994 | Yamazaki |
| 5,290,227 A | 1/1994 | Pasque |
| 5,360,445 A | 1/1994 | Goldowsky |
| 5,290,236 A | 3/1994 | Mathewson |
| 5,300,112 A | 4/1994 | Barr |
| 5,306,295 A | 4/1994 | Kolff et al. |
| 5,312,341 A | 5/1994 | Turi |
| 5,313,128 A | 5/1994 | Robinson et al. |
| 5,332,374 A | 7/1994 | Kricker et al. |
| 5,346,458 A | 9/1994 | Afield |
| 5,350,283 A | 9/1994 | Nakazeki et al. |
| 5,354,331 A | 11/1994 | Schachar |
| 5,370,509 A | 12/1994 | Golding et al. |
| 5,376,114 A | 12/1994 | Jarvik |
| 5,385,581 A | 1/1995 | Bramm et al. |
| 5,405,383 A | 11/1995 | Barr |
| 5,449,342 A | 12/1995 | Hirose et al. |
| 5,478,222 A | 12/1995 | Heidelberg et al. |
| 5,504,978 A | 4/1996 | Meyer, III |
| 5,507,629 A | 4/1996 | Jarvik |
| 5,519,270 A | 5/1996 | Yamada et al. |
| 5,533,957 A | 9/1996 | Aldea |
| 5,569,111 A | 10/1996 | Cho et al. |
| 5,575,630 A | 11/1996 | Nakazawa et al. |
| 5,588,812 A | 12/1996 | Taylor et al. |
| 5,595,762 A | 1/1997 | Derrieu et al. |
| 5,643,226 A | 1/1997 | Cosgrove et al. |
| 5,611,679 A | 3/1997 | Ghosh et al. |
| 5,613,935 A | 3/1997 | Jarvik |
| 5,678,306 A | 10/1997 | Bozeman, Jr. et al. |
| 5,692,882 A | 12/1997 | Bozeman, Jr. et al. |
| 5,695,471 A | 12/1997 | Wampler |
| 5,708,346 A | 1/1998 | Schob |
| 5,725,357 A | 3/1998 | Nakazeki et al. |
| 5,738,649 A | 4/1998 | Macoviak |
| 5,746,575 A | 5/1998 | Westphal et al. |
| 5,746,709 A | 5/1998 | Rom et al. |
| 5,755,784 A | 5/1998 | Jarvik |
| 5,776,111 A | 7/1998 | Tesio |
| 5,795,074 A | 8/1998 | Rahman et al. |
| 5,800,559 A | 9/1998 | Higham et al. |
| 5,807,311 A | 9/1998 | Palestrant |
| 5,814,011 A | 9/1998 | Corace |
| 5,824,069 A | 10/1998 | Lemole |
| 5,749,855 A | 12/1998 | Reitan |
| 5,843,129 A | 12/1998 | Larson et al. |
| 5,851,174 A | 12/1998 | Jarvik et al. |
| 5,853,394 A | 12/1998 | Tolkoff et al. |
| 5,890,883 A | 4/1999 | Golding et al. |
| 5,911,685 A | 6/1999 | Siess et al. |
| 5,917,295 A | 6/1999 | Mongeau |
| 5,917,297 A | 6/1999 | Gerster et al. |
| 5,921,913 A | 7/1999 | Siess |
| 5,924,848 A | 7/1999 | Izraelev |
| 5,924,975 A | 7/1999 | Goldowsky |
| 5,928,131 A | 7/1999 | Prem |
| 5,938,412 A | 8/1999 | Israelev |
| 5,941,813 A | 8/1999 | Sievers et al. |
| 5,945,753 A | 8/1999 | Maegawa et al. |
| 5,868,702 A | 9/1999 | Stevens et al. |
| 5,868,703 A | 9/1999 | Bertolero et al. |
| 5,947,703 A | 9/1999 | Nojiri et al. |
| 5,951,263 A | 9/1999 | Taylor et al. |
| 5,984,892 A | 11/1999 | Bedingham |
| 5,964,694 A | 12/1999 | Siess et al. |
| 6,004,269 A | 12/1999 | Crowley et al. |
| 6,007,479 A | 12/1999 | Rottenberg et al. |
| 6,030,188 A | 2/2000 | Nojiri et al. |
| 6,042,347 A | 3/2000 | Scholl et al. |
| 6,053,705 A | 4/2000 | Schob et al. |
| 6,066,086 A | 5/2000 | Antaki et al. |
| 6,071,093 A | 6/2000 | Hart |
| 6,074,180 A | 6/2000 | Khanwilkar et al. |
| 6,080,133 A | 6/2000 | Wampler |
| 6,082,900 A | 7/2000 | Takeuchi et al. |
| 6,083,260 A | 7/2000 | Aboul-Hosn et al. |
| 6,100,618 A | 8/2000 | Schoeb et al. |
| 6,058,593 A | 9/2000 | Siess |
| 6,123,659 A | 9/2000 | leBlanc et al. |
| 6,123,726 A | 9/2000 | Mori et al. |
| 6,139,487 A | 10/2000 | Siess |
| 6,086,527 A | 11/2000 | Talpade |
| 6,142,752 A | 11/2000 | Akamatsu et al. |
| 6,143,025 A | 11/2000 | Stobie et al. |
| 6,146,325 A | 11/2000 | Lewis et al. |
| 6,149,683 A | 11/2000 | Lancisi et al. |
| 6,158,984 A | 12/2000 | Cao et al. |
| 6,171,078 B1 | 1/2001 | Schob |
| 6,176,822 B1 | 1/2001 | Nix et al. |
| 6,176,848 B1 | 1/2001 | Rau et al. |
| 6,179,773 B1 | 1/2001 | Prem et al. |
| 6,190,304 B1 | 2/2001 | Downey et al. |
| 6,200,260 B1 | 3/2001 | Bolling |
| 6,206,659 B1 | 3/2001 | Izraelev |

(56) References Cited

U.S. PATENT DOCUMENTS

| | | |
|---|---|---|
| 6,254,359 B1 | 3/2001 | Aber |
| 6,222,290 B1 | 4/2001 | Schob et al. |
| 6,227,797 B1 | 5/2001 | Watterson et al. |
| 6,227,820 B1 | 5/2001 | Jarvik |
| 6,234,772 B1 | 5/2001 | Wampler et al. |
| 6,234,998 B1 | 5/2001 | Wampler |
| 6,247,892 B1 | 6/2001 | Kazatchkov et al. |
| 6,249,067 B1 | 6/2001 | Schob et al. |
| 6,264,635 B1 | 7/2001 | Wampler et al. |
| 6,268,675 B1 | 7/2001 | Amrhein |
| 6,276,831 B1 | 8/2001 | Takahashi et al. |
| 6,293,901 B1 | 9/2001 | Prem |
| 6,295,877 B1 | 10/2001 | Aboul-Hosn et al. |
| 6,319,231 B1 | 11/2001 | Andrulitis |
| 6,320,731 B1 | 11/2001 | Eeaves et al. |
| 6,245,007 B1 | 12/2001 | Bedingham et al. |
| 6,458,163 B1 | 1/2002 | Slemker et al. |
| 6,351,048 B1 | 2/2002 | Schob et al. |
| 6,355,998 B1 | 3/2002 | Schob et al. |
| 6,365,996 B2 | 4/2002 | Schob |
| 6,375,607 B1 | 4/2002 | Prem |
| 6,387,037 B1 | 5/2002 | Bolling et al. |
| 6,394,769 B1 | 5/2002 | Beamson et al. |
| 6,422,990 B1 | 7/2002 | Prem |
| 6,425,007 B1 | 7/2002 | Messinger |
| 6,428,464 B1 | 8/2002 | Bolling |
| 6,439,845 B1 | 8/2002 | Veres |
| 6,447,266 B2 | 9/2002 | Antaki et al. |
| 6,447,441 B1 | 9/2002 | Yu et al. |
| 6,508,777 B1 | 1/2003 | Macoviak et al. |
| 6,508,787 B2 | 1/2003 | Erbel et al. |
| 6,517,315 B2 | 2/2003 | Belady |
| 6,522,093 B1 | 2/2003 | Hsu et al. |
| 6,532,964 B2 | 3/2003 | Aboul-Hosn et al. |
| 6,533,716 B1 | 3/2003 | Schmitz-Rode et al. |
| 6,544,216 B1 | 4/2003 | Sammler et al. |
| 6,547,519 B2 | 4/2003 | deBlanc et al. |
| 6,547,530 B2 | 4/2003 | Ozaki et al. |
| 6,575,717 B2 | 6/2003 | Ozaki et al. |
| 6,589,030 B2 | 7/2003 | Ozaki |
| 6,595,762 B2 | 7/2003 | Khanwilkar et al. |
| 6,605,032 B2 | 8/2003 | Benkowski et al. |
| 6,609,883 B2 | 8/2003 | Woodard et al. |
| 6,610,004 B2 | 8/2003 | Viole et al. |
| 6,623,420 B2 | 9/2003 | Reich et al. |
| 6,641,378 B2 | 11/2003 | Davis et al. |
| 6,641,558 B1 | 11/2003 | Aboul-Hosn et al. |
| 6,688,861 B2 | 2/2004 | Wampler |
| 6,692,318 B2 | 2/2004 | McBride |
| 6,698,097 B1 | 3/2004 | Miura et al. |
| 6,709,418 B1 | 3/2004 | Aboul-Hosn et al. |
| 6,716,157 B2 | 4/2004 | Goldowsky |
| 6,716,189 B1 | 4/2004 | Jarvik et al. |
| 6,732,501 B2 | 5/2004 | Yu et al. |
| 6,749,598 B1 | 6/2004 | Keren et al. |
| 6,776,578 B2 | 8/2004 | Belady |
| 6,790,171 B1 | 9/2004 | Grundeman et al. |
| 6,794,789 B2 | 9/2004 | Siess et al. |
| 6,808,371 B2 | 10/2004 | Niwatsukino et al. |
| 6,817,836 B2 | 11/2004 | Nose et al. |
| 6,846,168 B2 | 1/2005 | Davis et al. |
| 6,860,713 B2 | 1/2005 | Hoover |
| 6,884,210 B2 | 4/2005 | Nose et al. |
| 6,935,344 B1 | 8/2005 | Aboul-Hosn et al. |
| 6,926,662 B1 | 9/2005 | Aboul-Hosn et al. |
| 6,942,672 B2 | 9/2005 | Heilman et al. |
| 6,949,066 B2 | 9/2005 | Beamson et al. |
| 6,966,748 B2 | 11/2005 | Woodard et al. |
| 6,974,436 B1 | 12/2005 | Aboul-Hosn et al. |
| 6,991,595 B2 | 1/2006 | Burke et al. |
| 7,010,954 B2 | 3/2006 | Siess et al. |
| 7,011,620 B1 | 3/2006 | Siess |
| 7,022,100 B1 | 4/2006 | Aboul-Hosn et al. |
| 7,048,681 B2 | 5/2006 | Tsubouchi et al. |
| 7,089,059 B1 | 8/2006 | Pless |
| 7,090,401 B2 | 8/2006 | Rahman et al. |
| 7,112,903 B1 | 9/2006 | Schob |
| 7,122,019 B1 | 10/2006 | Kesten et al. |
| 7,128,538 B2 | 10/2006 | Tsubouchi et al. |
| 7,027,875 B2 | 11/2006 | Siess et al. |
| 7,156,802 B2 | 1/2007 | Woodard et al. |
| 7,160,243 B2 | 1/2007 | Medvedev |
| 7,175,588 B2 | 2/2007 | Morello |
| 7,202,582 B2 | 4/2007 | Eckert et al. |
| 7,172,551 B2 | 6/2007 | Leasure |
| 7,241,257 B1 | 10/2007 | Ainsworth et al. |
| 7,284,956 B2 | 10/2007 | Nose et al. |
| 7,331,921 B2 | 2/2008 | Viole et al. |
| 7,335,192 B2 | 2/2008 | Keren et al. |
| 7,393,181 B2 | 7/2008 | McBride et al. |
| 7,431,688 B2 | 10/2008 | Wampler et al. |
| 7,329,236 B2 | 12/2008 | Kesten et al. |
| 7,462,019 B1 | 12/2008 | Allarie et al. |
| 7,467,930 B2 | 12/2008 | Ozaki et al. |
| 7,470,246 B2 | 12/2008 | Mori et al. |
| 7,476,077 B2 | 1/2009 | Woodard et al. |
| 7,491,163 B2 | 2/2009 | Viole et al. |
| 7,575,423 B2 | 8/2009 | Wampler |
| 7,645,225 B2 | 1/2010 | Medvedev et al. |
| 7,660,635 B1 | 2/2010 | Verness et al. |
| 7,699,586 B2 | 4/2010 | LaRose et al. |
| 7,748,964 B2 | 7/2010 | Yaegashi et al. |
| 7,731,675 B2 | 8/2010 | Aboul-Hosn et al. |
| 7,802,966 B2 | 9/2010 | Wampler et al. |
| 7,841,976 B2 | 11/2010 | McBride et al. |
| 7,862,501 B2 | 1/2011 | Woodard |
| 7,888,242 B2 | 2/2011 | Tanaka et al. |
| 7,934,909 B2 | 5/2011 | Nuesser et al. |
| 7,972,122 B2 | 7/2011 | LaRose et al. |
| 7,976,271 B2 | 7/2011 | LaRose et al. |
| 7,997,854 B2 | 8/2011 | LaRose et al. |
| 8,007,254 B2 | 8/2011 | LaRose et al. |
| 8,096,935 B2 | 1/2012 | Sutton et al. |
| 8,123,669 B2 | 2/2012 | Siess et al. |
| 8,152,493 B2 | 4/2012 | LaRose et al. |
| 8,177,703 B2 | 5/2012 | Smith et al. |
| 8,226,373 B2 | 7/2012 | Yaehashi |
| 8,282,359 B2 | 10/2012 | Ayre et al. |
| 8,283,829 B2 | 10/2012 | Yamamoto et al. |
| 8,366,381 B2 | 2/2013 | Woodard et al. |
| 8,403,823 B2 | 3/2013 | Yu et al. |
| 8,512,012 B2 | 8/2013 | Mustafa et al. |
| 8,535,211 B2 | 9/2013 | Campbell et al. |
| 8,585,290 B2 | 11/2013 | Bauer |
| 8,686,674 B2 | 4/2014 | Bi et al. |
| 8,770,945 B2 | 7/2014 | Ozaki et al. |
| 8,821,365 B2 | 9/2014 | Ozaki et al. |
| 8,827,661 B2 | 9/2014 | Mori |
| 8,652,024 B1 | 10/2014 | Yanai et al. |
| 8,864,644 B2 | 10/2014 | Yomtov |
| 8,870,552 B2 | 10/2014 | Ayre et al. |
| 8,968,174 B2 | 3/2015 | Yanai et al. |
| 9,039,595 B2 | 5/2015 | Ayre et al. |
| 9,067,005 B2 | 6/2015 | Ozaki et al. |
| 9,068,572 B2 | 6/2015 | Ozaki et al. |
| 9,109,601 B2 | 8/2015 | Mori |
| 9,132,215 B2 | 9/2015 | Ozaki et al. |
| 9,133,854 B2 | 9/2015 | Okawa et al. |
| 9,371,826 B2 | 6/2016 | Yanai et al. |
| 9,381,285 B2 | 7/2016 | Ozaki et al. |
| 9,382,908 B2 | 7/2016 | Ozaki et al. |
| 9,410,549 B2 | 8/2016 | Ozaki et al. |
| 9,556,873 B2 | 1/2017 | Yanai et al. |
| 9,713,663 B2 | 7/2017 | Medvedev et al. |
| 10,052,420 B2 | 8/2018 | Medvedev et al. |
| 10,506,935 B2 | 12/2019 | Medvedev et al. |
| 2001/0039369 A1 | 11/2001 | Terentiev |
| 2002/0051711 A1 | 5/2002 | Ozaki |
| 2002/0058994 A1 | 5/2002 | Hill et al. |
| 2002/0094281 A1 | 7/2002 | Khanwilkar et al. |
| 2002/0095210 A1 | 7/2002 | Finnegan et al. |
| 2003/0023302 A1 | 1/2003 | Moe et al. |
| 2003/0045772 A1 | 3/2003 | Reich et al. |
| 2003/0072656 A1 | 4/2003 | Niwatsukino et al. |

(56) References Cited

U.S. PATENT DOCUMENTS

| | | |
|---|---|---|
| 2003/0144574 A1 | 7/2003 | Heilman et al. |
| 2003/0199727 A1 | 10/2003 | Burke |
| 2003/0236488 A1 | 12/2003 | Novak |
| 2003/0236490 A1 | 12/2003 | Novak |
| 2004/0007515 A1 | 1/2004 | Geyer |
| 2004/0015232 A1 | 1/2004 | Shu et al. |
| 2004/0024285 A1 | 2/2004 | Muckter |
| 2004/0030381 A1 | 2/2004 | Shu |
| 2004/0064012 A1 | 4/2004 | Yanai |
| 2004/0143151 A1 | 7/2004 | Mori et al. |
| 2004/0145337 A1 | 7/2004 | Morishita |
| 2004/0152944 A1 | 8/2004 | Medvedev et al. |
| 2004/0171905 A1 | 9/2004 | Yu et al. |
| 2004/0210305 A1 | 10/2004 | Shu et al. |
| 2004/0215050 A1 | 10/2004 | Morello |
| 2004/0263341 A1 | 12/2004 | Enzinna |
| 2005/0004418 A1 | 1/2005 | Morello |
| 2005/0008496 A1 | 1/2005 | Tsubouchi et al. |
| 2005/0025630 A1 | 2/2005 | Ayre et al. |
| 2005/0043665 A1 | 2/2005 | Vinci et al. |
| 2005/0073273 A1 | 4/2005 | Maslov et al. |
| 2005/0089422 A1 | 4/2005 | Ozaki et al. |
| 2005/0131271 A1 | 6/2005 | Benkowski et al. |
| 2005/0141887 A1 | 6/2005 | Lelkes |
| 2005/0194851 A1 | 9/2005 | Eckert et al. |
| 2005/0261542 A1 | 11/2005 | Abe et al. |
| 2005/0287022 A1 | 12/2005 | Yaegashi et al. |
| 2006/0024182 A1 | 2/2006 | Akdis et al. |
| 2006/0055274 A1 | 3/2006 | Kim |
| 2006/0127227 A1 | 6/2006 | Mehlhorn et al. |
| 2007/0073393 A1 | 3/2007 | Kung et al. |
| 2007/0078293 A1 | 4/2007 | Shambaugh, Jr. |
| 2007/0095648 A1 | 5/2007 | May et al. |
| 2007/0114961 A1 | 5/2007 | Schwarzkopf |
| 2007/0134993 A1 | 6/2007 | Tamez et al. |
| 2007/0189648 A1 | 8/2007 | Kita et al. |
| 2007/0213690 A1 | 9/2007 | Phillips et al. |
| 2007/0231135 A1 | 10/2007 | Wampler et al. |
| 2007/0282298 A1 | 12/2007 | Mason |
| 2007/0297923 A1 | 12/2007 | Tada |
| 2008/0007196 A1 | 1/2008 | Tan et al. |
| 2008/0021394 A1 | 1/2008 | La Rose et al. |
| 2008/0030895 A1 | 2/2008 | Obara et al. |
| 2008/0119777 A1 | 5/2008 | Vinci et al. |
| 2008/0124231 A1 | 5/2008 | Yaegashi |
| 2008/0183287 A1 | 7/2008 | Ayre |
| 2008/0211439 A1 | 9/2008 | Yokota et al. |
| 2008/0281146 A1 | 11/2008 | Morello |
| 2009/0041595 A1 | 2/2009 | Garzaniti et al. |
| 2009/0060743 A1 | 3/2009 | McBride et al. |
| 2009/0074336 A1 | 3/2009 | Engesser et al. |
| 2009/0099406 A1 | 4/2009 | Salmonsen et al. |
| 2009/0171136 A1 | 7/2009 | Shambaugh, Jr. |
| 2009/0257693 A1 | 10/2009 | Aiello |
| 2009/0318834 A1 | 12/2009 | Fujiwara et al. |
| 2010/0185280 A1 | 6/2010 | Ayre et al. |
| 2010/0168534 A1 | 7/2010 | Matsumoto et al. |
| 2010/0222634 A1 | 9/2010 | Poirier |
| 2010/0234835 A1 | 9/2010 | Horikawa et al. |
| 2010/0256440 A1 | 10/2010 | Maher |
| 2010/0262039 A1 | 10/2010 | Fujiwara et al. |
| 2010/0266423 A1 | 10/2010 | Gohean et al. |
| 2010/0268333 A1 | 10/2010 | Gohean et al. |
| 2010/0305692 A1 | 12/2010 | Thomas et al. |
| 2010/0324465 A1 | 12/2010 | Vinci et al. |
| 2011/0015732 A1 | 1/2011 | Kanebako |
| 2011/0077531 A1 | 3/2011 | Watson et al. |
| 2011/0112354 A1 | 5/2011 | Nishimura et al. |
| 2011/0118766 A1 | 5/2011 | Reichenbach et al. |
| 2011/0118829 A1 | 5/2011 | Hoarau et al. |
| 2011/0118833 A1 | 5/2011 | Reichenbach et al. |
| 2011/0129373 A1 | 6/2011 | Mori |
| 2011/0160519 A1 | 6/2011 | Arndt et al. |
| 2011/0218383 A1 | 9/2011 | Broen et al. |
| 2011/0218384 A1 | 9/2011 | Bachman et al. |
| 2011/0218385 A1 | 9/2011 | Bolyare et al. |
| 2011/0237978 A1 | 9/2011 | Fujiwara et al. |
| 2011/0243759 A1 | 10/2011 | Ozaki et al. |
| 2011/0318203 A1 | 12/2011 | Ozaki et al. |
| 2012/0003108 A1 | 1/2012 | Ozaki et al. |
| 2012/0016178 A1 | 1/2012 | Woodard et al. |
| 2012/0022645 A1 | 1/2012 | Burke |
| 2012/0035411 A1 | 2/2012 | LaRose et al. |
| 2012/0078030 A1 | 3/2012 | Bourque |
| 2012/0078031 A1 | 3/2012 | Burke et al. |
| 2012/0095281 A1 | 4/2012 | Reichenbach et al. |
| 2012/0130152 A1 | 5/2012 | Ozaki et al. |
| 2012/0226350 A1 | 9/2012 | Ruder et al. |
| 2012/0243759 A1 | 9/2012 | Fujisawa |
| 2012/0245681 A1 | 9/2012 | Casas et al. |
| 2012/0253103 A1 | 10/2012 | Jarvik |
| 2012/0308363 A1 | 12/2012 | Ozaki et al. |
| 2013/0030240 A1 | 1/2013 | Schima et al. |
| 2013/0121821 A1 | 5/2013 | Ozaki et al. |
| 2013/0158521 A1 | 6/2013 | Sobue |
| 2013/0170970 A1 | 7/2013 | Ozaki et al. |
| 2013/0178694 A1 | 7/2013 | Jeffery et al. |
| 2013/0225909 A1 | 8/2013 | Dormanen et al. |
| 2013/0243623 A1 | 9/2013 | Okawa et al. |
| 2013/0289334 A1 | 10/2013 | Badstibner et al. |
| 2013/0331711 A1 | 12/2013 | Mathur et al. |
| 2014/0030122 A1 | 1/2014 | Ozaki et al. |
| 2014/0066690 A1 | 3/2014 | Siebenhaar et al. |
| 2014/0066691 A1 | 3/2014 | Siebenhaar |
| 2014/0100413 A1 | 4/2014 | Casas et al. |
| 2014/0107399 A1 | 4/2014 | Spence |
| 2014/0142367 A1 | 5/2014 | Ayre et al. |
| 2014/0155682 A1 | 6/2014 | Jeffery et al. |
| 2014/0200389 A1 | 7/2014 | Yanai et al. |
| 2014/0205467 A1 | 7/2014 | Yanai et al. |
| 2014/0241904 A1 | 8/2014 | Yanai et al. |
| 2014/0275721 A1 | 9/2014 | Yanai et al. |
| 2014/0275727 A1 | 9/2014 | Bonde et al. |
| 2014/0296615 A1 | 10/2014 | Franano |
| 2014/0309481 A1 | 10/2014 | Medvedev et al. |
| 2014/0314597 A1 | 10/2014 | Allaire et al. |
| 2014/0323796 A1 | 10/2014 | Medvedev et al. |
| 2014/0343352 A1 | 11/2014 | Ardt et al. |
| 2015/0017030 A1 | 1/2015 | Ozaki |
| 2015/0023803 A1 | 1/2015 | Fritz et al. |
| 2015/0057488 A1 | 2/2015 | Yomtov |
| 2015/0078936 A1 | 3/2015 | Mori |
| 2015/0306290 A1 | 10/2015 | Rosenberg et al. |
| 2015/0367048 A1 | 12/2015 | Brown et al. |
| 2015/0374892 A1 | 12/2015 | Yanai et al. |
| 2016/0058929 A1 | 3/2016 | Medvedev et al. |
| 2016/0058930 A1 | 3/2016 | Medvedev et al. |
| 2016/0235898 A1 | 8/2016 | Yanai et al. |
| 2016/0235899 A1 | 8/2016 | Yu et al. |
| 2016/0235900 A1 | 8/2016 | Yanai et al. |
| 2016/0281720 A1 | 9/2016 | Yanai et al. |
| 2016/0281728 A1 | 9/2016 | Ozaki et al. |

FOREIGN PATENT DOCUMENTS

| | | |
|---|---|---|
| CN | 102239334 A | 11/2011 |
| CN | 102341600 A | 2/2012 |
| EP | 2945662 B1 | 9/1999 |
| EP | 971212 A | 1/2000 |
| EP | 1113117 A2 | 7/2001 |
| EP | 1327455 A | 7/2003 |
| EP | 1430919 A1 | 6/2004 |
| EP | 1495773 A2 | 1/2005 |
| EP | 1495773 A3 | 1/2005 |
| EP | 1598087 A2 | 3/2005 |
| EP | 1526286 A2 | 4/2005 |
| EP | 1495773 B1 | 2/2009 |
| EP | 2292282 A1 | 3/2011 |
| EP | 2298375 A1 | 3/2011 |
| EP | 2372160 A1 | 10/2011 |
| EP | 2405140 A1 | 1/2012 |
| EP | 2405141 A1 | 1/2012 |
| EP | 2461465 A1 | 6/2012 |
| EP | 2538086 A1 | 12/2012 |

(56) References Cited

FOREIGN PATENT DOCUMENTS

| | | |
|---|---|---|
| EP | 2554191 A1 | 2/2013 |
| EP | 2594799 A1 | 5/2013 |
| EP | 2618001 A1 | 7/2013 |
| EP | 2693609 A1 | 2/2014 |
| EP | 2948202 A1 | 12/2015 |
| EP | 2961987 A1 | 1/2016 |
| EP | 3013385 A2 | 5/2016 |
| JP | 58-9535 | 1/1983 |
| JP | 61-293146 | 12/1986 |
| JP | H02-007780 U | 1/1990 |
| JP | H02-033590 U | 3/1990 |
| JP | 04-091396 A | 3/1992 |
| JP | 04-148094 A | 5/1992 |
| JP | 05-021197 U | 3/1993 |
| JP | 06-014538 U | 2/1994 |
| JP | 06-053790 U | 7/1994 |
| JP | 2006-070476 U | 9/1994 |
| JP | 2006-245455 | 9/1994 |
| JP | 07-014220 U | 3/1995 |
| JP | 07-042869 U | 8/1995 |
| JP | 07-509156 A | 10/1995 |
| JP | 09-122228 A | 5/1997 |
| JP | 10-331841 A | 12/1998 |
| JP | 11-244377 A | 9/1999 |
| JP | 2001-309628 | 11/2001 |
| JP | 2003-135592 A | 5/2003 |
| JP | 2004-166401 A | 6/2004 |
| JP | 2004-209240 A | 7/2004 |
| JP | 2004-332566 A | 11/2004 |
| JP | 2004-346925 A | 12/2004 |
| JP | 2005-094955 | 4/2005 |
| JP | 2005-127222 A | 5/2005 |
| JP | 2005-245138 | 9/2005 |
| JP | 2005-270345 A | 10/2005 |
| JP | 2005-270415 A | 10/2005 |
| JP | 2005-287599 A | 10/2005 |
| JP | 2006-167173 A | 6/2006 |
| JP | 2007-002885 A | 1/2007 |
| JP | 2007-043821 | 2/2007 |
| JP | 2007-089972 A | 4/2007 |
| JP | 2007-089974 | 4/2007 |
| JP | 2007-215292 | 8/2007 |
| JP | 2007-247489 | 9/2007 |
| JP | 2008-011611 | 1/2008 |
| JP | 2008-104278 | 5/2008 |
| JP | 2008-132131 | 6/2008 |
| JP | 2008-99453 | 8/2008 |
| JP | 2008-193838 | 8/2008 |
| JP | 2008-297997 A | 12/2008 |
| JP | 2008-301634 | 12/2008 |
| JP | 2006-254619 | 9/2009 |
| JP | 2010-133381 A | 6/2010 |
| JP | 2010-136863 A | 6/2010 |
| JP | 2010-203398 A | 9/2010 |
| JP | 2010-209691 A | 9/2010 |
| JP | 2011-169166 A | 9/2011 |
| JP | 2012-021413 A | 2/2012 |
| JP | 2012-062790 A | 3/2012 |
| JP | 5171953 B2 | 3/2013 |
| JP | 5572832 B2 | 8/2014 |
| JP | 5656835 B2 | 1/2015 |
| WO | 1993-07388 A1 | 4/1993 |
| WO | 94-14226 | 6/1994 |
| WO | 1996-31934 | 10/1996 |
| WO | 1997-42413 A1 | 11/1997 |
| WO | 2000-64509 A1 | 11/2000 |
| WO | 2004-098677 A1 | 11/2004 |
| WO | 2005-011087 A1 | 2/2005 |
| WO | 2005-028000 A1 | 3/2005 |
| WO | 2005-034312 A2 | 4/2005 |
| WO | 2009-157408 A1 | 12/2009 |
| WO | 2010-067682 A1 | 6/2010 |
| WO | 2010-101082 A1 | 9/2010 |
| WO | 2010-101107 A1 | 9/2010 |
| WO | 2011-013483 A1 | 2/2011 |
| WO | 2012-036059 A1 | 3/2012 |
| WO | 2012-040544 A1 | 3/2012 |
| WO | 2012-047550 A1 | 4/2012 |
| WO | 2012-132850 A1 | 10/2012 |
| WO | 2014-113533 A1 | 7/2014 |
| WO | 2014-116676 A1 | 7/2014 |
| WO | 2014-133942 A1 | 9/2014 |
| WO | 2014-179271 A2 | 11/2014 |
| WO | 2016-033131 A1 | 3/2016 |
| WO | 2016-033133 A1 | 3/2016 |
| WO | 2016-130944 A1 | 8/2016 |
| WO | 2016-130955 A1 | 8/2016 |
| WO | 2016-130989 A1 | 8/2016 |

OTHER PUBLICATIONS

Extended European Search Report dated Nov. 19, 2012, in European Patent Application No. 10748677.1, all pages.
Extended European Search Report dated Jun. 18, 2015, in European Patent Application No. 11825062.0, all pages.
Extended European Search Report dated Oct. 8, 2014, in European Patent Application No. 11806627.3, all pages.
Extended European Search Report dated Apr. 2, 2015, in European Patent Application No. 09770118.9 filed Jun. 22, 2009, all pages.
Extended European Search Report dated Feb. 4, 2016 in European Patent Application No. 12764433.4, all pages.
Extended European Search report dated Sep. 8, 2016 in European Patent Application No. 14741174, all pages.
Extended European Search Report dated Sep. 29, 2016 in European Patent Application No. 14743371, all pages.
Supplementary European Search Report dated Jan. 7, 2013, in European Application No. 09831788.6, 7 pages.
Office Action dated Jan. 27, 2016 in European Patent Application No. 10804230.0, all pages.
Office Action dated Jul. 22, 2016 in European Patent Application No. 09770118.9, all pages.
Office Action dated Oct. 31, 2016 in European Patent Application No. 10804230.0, all pages.
Office Action dated Jul. 19, 2016, in European Patent Application No. 11825062.0 all pages.
Office Action dated Dec. 11, 2015 in Japanese Patent Application No. 2013-507344, all pages.
Notice of Decision to Grant dated Jun. 15, 2016, in Japanese Patent Application No. 2013-507344, all pages.
International Search Report and Written Opinion dated Jul. 14, 2009 in International Patent Application No. PCT/JP2009/061318 filed Jun. 22, 2009, all pages.
International Search Report and Written Opinion dated Apr. 12, 2011, in International Patent Application No. PCT/JP2011/050925 filed Jan. 20, 2011, all pages.
International Search Report and Written Opinion dated Apr. 12, 2011 in International Patent Application No. PCT/JP2011/054134, filed Feb. 24, 2011, all pages.
International Search Report and Written Opinion dated Sep. 13, 2011 in International Patent Application No. PCT/JP2011/064768, filed Jun. 28, 2011, all pages.
International Search Report and Written Opinion dated Dec. 13, 2011 in International Patent Application No. PCT/JP2011/070450, filed Sep. 8, 2011, all pages.
International Search Report and Written Opinion dated Feb. 19, 2014 in International Patent Application No. PCT/US2014/012448, filed Jan. 22, 2014, all pages.
International Search Report and Written Opinion dated May 5, 2014, in International Patent Application No. PCT/US2014/011786, filed Jan. 16, 2014, all pages.
International Preliminary Report on Patentability dated Jul. 30, 2015 for International Patent Application No. PCT/US2014/011786, filed on Jan. 16, 2014, all pages.
International Search Report and Written Opinion dated May 9, 2014, in International Patent Application No. PCT/US2014/012502, filed Jan. 22, 2014, all pages.

(56) References Cited

OTHER PUBLICATIONS

International Preliminary Report on Patentability dated Aug. 6, 2015 for International Patent Application No. PCT/US2014/012502 filed on Jan. 22, 2014, all pages.
International Search Report and Written Opinion dated May 14, 2014 in International Patent Application No. PCT/US2014/012511, filed Jan. 22, 2014, all pages.
International Preliminary Report on Patentability dated Aug. 6, 2015 for International Patent Application No. PCT/US2014/012511 filed on Jan. 22, 2014, all pages.
International Search Report and Written Opinion dated Jun. 16, 2014 in International Patent Application No. PCT/US2014/017932, filed Feb. 24, 2014, all pages.
International Preliminary Report on Patentability dated Sep. 11, 2015 in International Patent Application No. PCT/US2014/017932, filed Feb. 24, 2014, all pages.
International Search Report and Written Opinion dated Feb. 11, 2016, in International Patent Application No. PCT/US2014/035798, filed Apr. 29, 2014, all pages.
International Preliminary Report on Patentability dated Feb. 25, 2016 in International Patent Application No. PCT/US2014/035798, filed on Apr. 29, 2014, all pages.
International Search Report and Written Opinion dated May 16, 2016, in International Patent Application No. PCT/US2016/017611, all pages.
International Search Report and Written Opinion dated May 16, 2016, in International Patent Application No. PCT/US2016/017791, all pages.
International Search Report and Written Opinion dated Jun. 7, 2016, in International Patent Application No. PCT/US2016/017812, all pages.
International Search Report and Written Opinion dated Jun. 8, 2016, in International Patent Application No. PCT/US2016/017864, all pages.
International Search Report and Written Opinion dated Oct. 27, 2015, in International Patent Application No. PCT/US2015/046844, all pages.
International Search Report and Written Opinion dated Oct. 27, 2015, in International Patent Application No. PCT/US2015/046846, all pages.
International Search Report and Written Opinion dated Feb. 24, 2017, in International Patent Application No. PCT/US2016/062284, all pages.
Asama, J., et al., "A Compact Highly Efficient and Low Hemolytic Centrifugal Blood Pump With a Magnetically Levitated Impeller", Artificial Organs, vol. 30, No. 3, Mar. 1, 2006, pp. 160-167.
Asama, J., et al., "A New Design for a Compact Centrifugal Blood Pump with a Magnetically Levitated Rotor", Asaio Journal, vol. 50, No. 6, Nov. 1, 2004, pp. 550-556.
Asama, J., et al., "Suspension Performance of a Two-Axis Actively Regulated Consequent-Pole Bearingless Motor," IEEE Transactions on Energy Conversion, vol. 28, No. 4, Dec. 2013, 8 pages.
Kosaka, R., et al., "Operating Point Control System for a Continuous Flow Artificial Heart: In Vitro Study," ASAIO Journal 2003, vol. 49, DOI:10.1097/01.MAT.0000065376.28871.A8, pp. 259-264.
Neethu, S., et al., "Novel design, optimization and realization of axial flux motor for implantable blood pump", Power Electronics, Drives and Energy Systems (PEDES) & 2010 Power Indian, 2010 Joint International Conference on, IEEE, Dec. 20, 2010 (Dec. 20, 2010), pp. 1-6.
Sandtner, J., et al., "Electrodynamic Passive Magnetic Bearing with Planar Halbach Arrays", Ninth International Symposium on Magnetic Bearings, Aug. 3-6, 2004, retrieved from the internet: <http://www.silphenix.ch/lexington.pdf>, all pages.
Terumo Heart, Inc., "Handled With Care—Significantly Reduce the Risk of Cell Damage," Terumo brochure, Apr. 2010, 2 pages.
Yamazaki, K., et al., "Development of a Miniature Intraventricular Axial Flow Blood Pump," ASAIO Journal, 1993, vol. 39, pp. M224-M230.
Gieras, et al., "Advancements in Electric Machines—2.5 Permanent Magnets", Nov. 14, 2008, pp. 43-48.

| Cases | Timing Figure | Initial speed synchronization start point | Conditions to use this case |
|---|---|---|---|
| Case 1: Maximum time point as the reference | (waveform with labels A, D, C, E, F, B) | $t_{sync}[0] = t_{max}[i] + T_{cyc}[i] - T_{sp}$<br><br>Here, $T_{sp}$ is the duration of speed synchronization | When $T_{max2max}[i]$ is most close to $T_{cyc}[i]$ |
| Case 2: Minimum time point as the reference | (waveform with labels A, D, C, J, G, H, E, F, B) | $t_{sync}[0] = t_{min}[i] + T_{cyc}[i] + T_{k1}$<br><br>Here, $T_{k1} = k_1 T_{min2max}$, $k_1 \approx 0.25$ to $0.4$, which depends on the $T_{sp}$ | When $T_{min2min}[i]$ is most close to $T_{cyc}[i]$ |

A = Filtered Motor Drive Current or Power
B = Speed Reference
C = $T_{cyc}[i]$
D = $T_{max}[i]$
E = $t_{sync}[0]$
F = $T_{sp}$ G = $T_{min}[i]$
H = $T_{min2max}[i]$
J = $T_{k1}$
K = $T_{f2min}[i]$
L = $T_f[i]$
M = $T_f[i+1]$ N = $T_{f2min}$
P = $T_{cyc}[i]$
Q = $T_r[i]$
R = $T_{k2}$

FIG. 6A

| Cases | Timing Figure | Initial speed synchronization start point | Conditions to use this case |
|---|---|---|---|
| Case 3: Falling-crossing time point as the reference | (waveform with labels A, K, L, M, N, J, E, F, B) | $t_{sync}[0] = t_f[i+1] + \tau_{f2min} + T_{k1}$<br><br>Here, $\tau_{f2min}$ is average of $T_{f2min}$, $T_{k1}$ is same as the case 2 | When $T_{f2f}[i]$ is most close to $T_{cyc}[i]$ |
| Case 4: Rising-crossing time point as the reference | (waveform with labels A, P, Q, R, E, F, B) | $t_{sync}[0] = t_r[i] + T_{cyc}[i] - T_{k2}$<br><br>Here $T_{k2} = k_2 T_{min2max}, k_2 \approx 0.125$ to $0.3$, which depends on the $T_{sp}$ | When $T_{r2r}[i]$ is most close to $T_{cyc}[i]$ |

A = Filtered Motor Drive Current or Power  
B = Speed Reference  
C = $T_{cyc}[i]$  
D = $T_{max}[i]$  
E = $t_{sync}[0]$  
F = $T_{sp}$ G = $T_{min}[i]$  
H = $T_{min2max}[i]$  
J = $T_{k1}$  
K = $T_{f2min}[i]$  
L = $T_f[i]$  
M = $T_f[i+1]$ N = $T_{f2min}$  
P = $T_{cyc}[i]$  
Q = $T_r[i]$  
R = $T_{k2}$

FIG. 6B

HEART BEAT IDENTIFICATION AND PUMP SPEED SYNCHRONIZATION

CROSS-REFERENCE TO RELATED APPLICATIONS

This application is a continuation of U.S. patent application Ser. No. 16/050,889, filed Jul. 31, 2018, now U.S. Pat. No. 10,506,935 issued Dec. 17, 2019, and entitled "HEART BEAT IDENTIFICATION AND PUMP SPEED SYNCHRONIZATION," which is a continuation application of U.S. patent application Ser. No. 15/041,716, filed Feb. 11, 2016, now U.S. Pat. No. 10,052,420, issued Aug. 21, 2018, and entitled "HEART BEAT IDENTIFICATION AND PUMP SPEED SYNCHRONIZATION," which claims priority to U.S. Provisional Application No. 62/114,886, filed Feb. 11, 2015 and entitled "HEART BEAT IDENTIFICATION AND PUMP SPEED SYNCHRONIZATION." This application is also related to co-pending and commonly assigned U.S. patent application Ser. No. 13/873,551, filed Apr. 30, 2013, and entitled "CARDIAC PUMP WITH SPEED ADAPTED FOR VENTRICLE UNLOADING." These Applications are incorporated by reference herein in their entirety.

BACKGROUND OF THE INVENTION

A left ventricular assist device (LVAD) and/or other devices may be used to provide long-term support for heart failure patients or patients suffering from other heart related conditions. Traditionally, many such devices assist heart functioning by generating a continuous blood flow using a constant pumping speed set by clinician based on the patient's physiologic conditions at that time when the particular device is implanted.

However, the natural cardiac cycle of a human being (or other animals) does not usually generate a continuous and constant blood flow. Instead, flow is highest during the systole of a cardiac cycle, and then decreased during the diastole of the cardiac cycle. Thus the heart and the implanted device operate in different fashions (i.e., non-constant versus constant flow) which may be detrimental to the patient.

Embodiments of the present invention provide systems and methods for determining characteristics of a cardiac cycle, so that operation of LVAD and/or other devices may be altered in a dynamic manner when used in a human or other animal experiencing heart related conditions.

BRIEF SUMMARY OF THE INVENTION

In one aspect, a method for synchronizing operation of a heart assist pump device to a patient's cardiac cycle is provided. The method may include obtaining a signal from a motor of a heart assist pump device and filtering the signal to remove noise. The method may also include determining a speed synchronization start point at which time the motor of the heart assist pump device will begin a change in speed of operation based on the filtered signal. The method may further include modulating a speed of the motor of the heart assist pump device to a target speed at the speed synchronization start point, thereby synchronizing the change in speed of operation with a patient's cardiac cycle.

In another aspect, a heart assist pump device is provided. The device may include a motor and a controller. The controller may be configured to obtain frequency range data from the motor and to determine a speed synchronization start point at which time the motor of the heart assist pump device will begin a change in speed of operation based on the frequency range data. The controller may also be configured to modulate a speed of the motor to a target speed at the speed synchronization start point, thereby synchronizing the change in speed of operation with a patient's cardiac cycle.

BRIEF DESCRIPTION OF THE DRAWINGS

The present invention is described in conjunction with the appended figures:

FIGS. 6A and 6B show four possible ways to determine an initial speed synchronization start point.

DETAILED DESCRIPTION OF THE INVENTION

Figure 1:
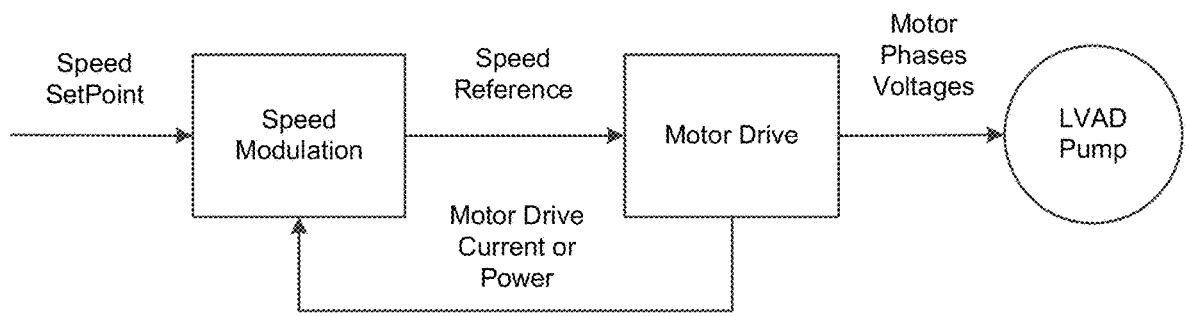
FIG. 1 shows a top level block diagram of a LVAD pump control system of one embodiment of the invention.

The ensuing description provides exemplary embodiments only, and is not intended to limit the scope, applicability or configuration of the disclosure. Rather, the ensuing description of the exemplary embodiments will provide those skilled in the art with an enabling description for implementing one or more exemplary embodiments. It being understood that various changes may be made in the function and arrangement of elements without departing from the spirit and scope of the invention as set forth herein.

Specific details are given in the following description to provide a thorough understanding of the embodiments. However, it will be understood by one of ordinary skill in the art that the embodiments may be practiced without these specific details. For example, with regard to any specific embodiment discussed herein, any one or more details may or may not be present in all versions of that embodiment. Likewise, any detail from one embodiment may or may not be present in any particular version of another embodiment discussed herein. Additionally, well-known circuits, systems, processes, algorithms, structures, and techniques may be shown without unnecessary detail in order to avoid obscuring the embodiments. The absence of discussion of any particular element with regard to any embodiment herein shall be construed to be an implicit contemplation by the disclosure of the absence of that element in any particular version of that or any other embodiment discussed herein.

Also, it is noted that individual embodiments may be described as a process which is depicted as a flowchart, a flow diagram, a data flow diagram, a structure diagram, or a block diagram. Although a flowchart may describe the operations as a sequential process, many of the operations can be performed in parallel or concurrently. In addition, the order of the operations may be re-arranged. A process may be terminated when its operations are completed, but could have additional steps not discussed or included in a figure. Furthermore, not all operations in any particularly described process may occur in all embodiments. A process may correspond to a method, a function, a procedure, a subroutine, a subprogram, etc. When a process corresponds to a function, its termination corresponds to a return of the function to the calling function or the main function.

The term "machine-readable medium" includes, but is not limited to portable or fixed storage devices, optical storage devices, wireless channels and various other mediums capable of storing, containing or carrying instructions and/or data. A code segment or machine-executable instructions may represent a procedure, a function, a subprogram, a program, a routine, a subroutine, a module, a software package, a class, or any combination of instructions, data structures, or program statements. A code segment may be coupled to another code segment or a hardware circuit by passing and/or receiving information, data, arguments, parameters, or memory contents. Information, arguments, parameters, data, etc. may be passed, forwarded, or transmitted via any suitable means including memory sharing, message passing, token passing, network transmission, etc.

Furthermore, embodiments of the invention may be implemented, at least in part, either manually or automatically. Manual or automatic implementations may be executed, or at least assisted, through the use of machines, hardware, software, firmware, middleware, microcode, hardware description languages, or any combination thereof. When implemented in software, firmware, middleware or microcode, the program code or code segments to perform the necessary tasks may be stored in a machine readable medium. One or more processors may perform the necessary tasks.

In some embodiments, a left ventricular assist device (LVAD) or other device may be intended to provide the long-term support for a heart failure patient or a patient suffering from another condition. Many such devices generate a continuous blood flow using a constant pumping speed set by clinician or other process based on the patient's physiologic conditions at that time when such device is implanted. However, there is the potential to vary the speed of the device to be synchronized to the natural cardiac cycle by modulating the speed based on the natural cardiac cycle. Using this approach, the pump speed is increased during systole of a cardiac cycle (the time of highest flow) and decreased during diastole (the time of lowest flow), so that a maximum unloading of a weakened ventricle may be obtained. This may establish stable hemodynamic conditions and enables a variation of the aortic pulse pressure, while keeping the organ perfusion at an even level to benefit the patient's recovery. Although the heart is weakened, it is still beating. The LVAD may support the beating heart such that when the heart pumps the resistance met by the pump goes down and vice versa. This would be seen as a change in the back emf and current. In some embodiments, the change in current may depend on the control scheme. For example, the LVAD may be designed to maintain a set motor speed (rpm). The current needed to maintain the speed goes down during pumping (systole). In other embodiments, the LVAD may be designed to maintain a set flow rate, causing the current to go down during systole. It will be appreciated that the LVAD could be designed to just apply a set current, in which case it doesn't matter what the heart is doing. The flow rate will then go up when the pump and heart are pushing fluid at the same time.

In some embodiments the pump speed of a LVAD or other device may be precisely synchronized to the systolic phases of the cardiac cycle in a reliable real-time mode regardless of the irregular heart beats. This may prevent a lack of synchrony which may cause ventricular load fluctuation or even overloading of the heart which can increase the occurrence of adverse events and affect the recovery of the patient. Unsynchronized increases in pump speed could also increase the risk of ventricular suction, particularly at the end of systole when the ventricle could be nearly empty. Embodiments of the invention reduce such risks by properly identifying regular heart beats and the proper time to increase pump speed relative thereto.

Embodiments of the invention implement real-time speed modulation to at least more precisely synchronize LVAD pumps or other devices with the heart beat cycle that allow for increasing the pump speed before the systolic phase and reducing the speed before the end of systole. FIG. 1 shows a top level block diagram of a LVAD pump control system (or control system for other device) with speed modulation. In this control system, motor drive current or power signal is used as the input of the speed modulation since it reflects the heart beat cycle pattern. By extracting the motor drive current or power signal features, speed synchronization time points within the heart beat cycles can be determined. Based on the speed synchronization time points, the speed set-point configured by clinician or other method can be modulated to the targeted speed reference automatically at the right time for a motor drive of a pump or other device to achieve the required synchronicity.

Figure 2:
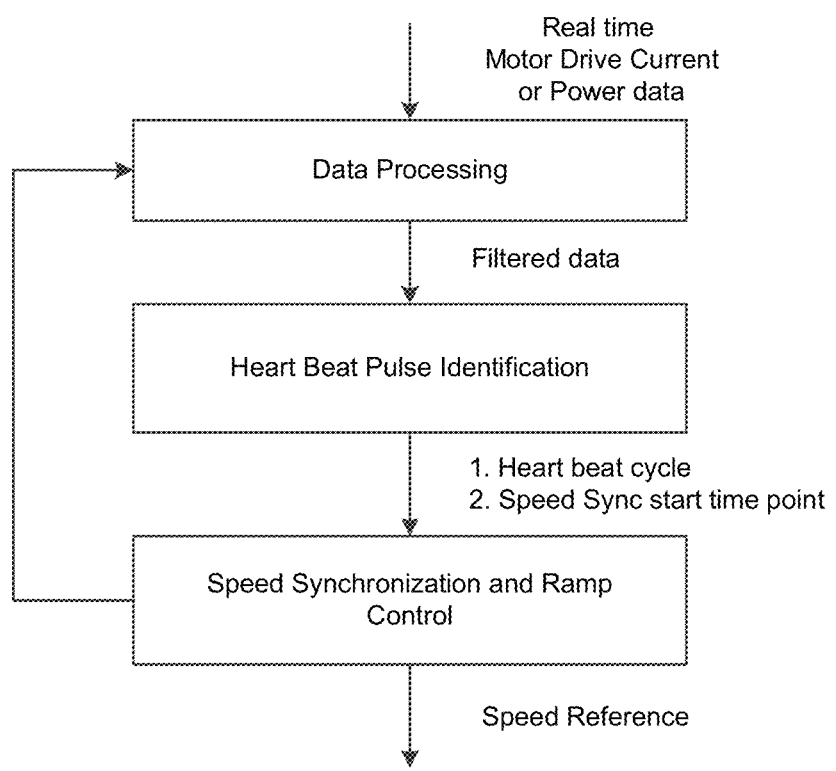
FIG. 2 shows one speed modulation architecture of one embodiment of the invention.

The architecture of speed modulation is shown in FIG. 2 which consists of three main stages:

Stage 1—Data Processing—A filter is employed to obtain reasonable frequency range data from the raw motor current or power signal data which is concurrent with, and representative of, the heart beat cycle.

Stage 2—Heart Beat Pulse Identification—The heart beat cycle features are identified from the filtered motor current or power data from Stage 1 to determines the speed synchronization start time point (i.e., the point in time in which the pump speed should increase).

Stage 3—Speed Synchronization and Ramp Control—Based on the speed synchronization start point identified in Stage 2, a pump motor is controlled to synchronize speed increases thereof with heart beats. A targeted speed reference for the motor drive, with ramp up and down control, is specified by a clinician or other method.

At Stage 1, high frequency noise data which is out of the general heart beat range (i.e. less than 5 Hz (300 beats/min)) is filtered out of the motor current or power data. Any kind of digital filter, for example, an infinite impulse response filter (IIR) or finite impulse response filter (FIR), may be employed, but the phase delay and computational load may need to be considered when implemented it into an embedded LVAD controller. In one embodiment, a second order IIR is employed.

At Stage 2, the pulse period of heart beat is identified from the filtered motor current or power data from Stage 1. In some embodiments, at least two consecutive and complete prior-occurring heart beats may be analyzed to anticipate the current heart beat cycle features. In other embodiments, the two complete prior-occurring heart beats may not be consecutive, or more than two complete prior-occurring heart beats may be analyzed, either consecutive or non-consecutive. In some embodiments, more than two complete prior-occurring heart beats may be analyzed. For example, three, four, five, or any specific number of heart beats greater than five may be analyzed depending on the embodiment. However, using more than the last two consecutive and complete prior-occurring heart beats may involve older heart beat history data which may include irregular heart beats or inconsistent data, thereby reducing the accuracy of the predicted current heart beats cycle features.

Figure 3:
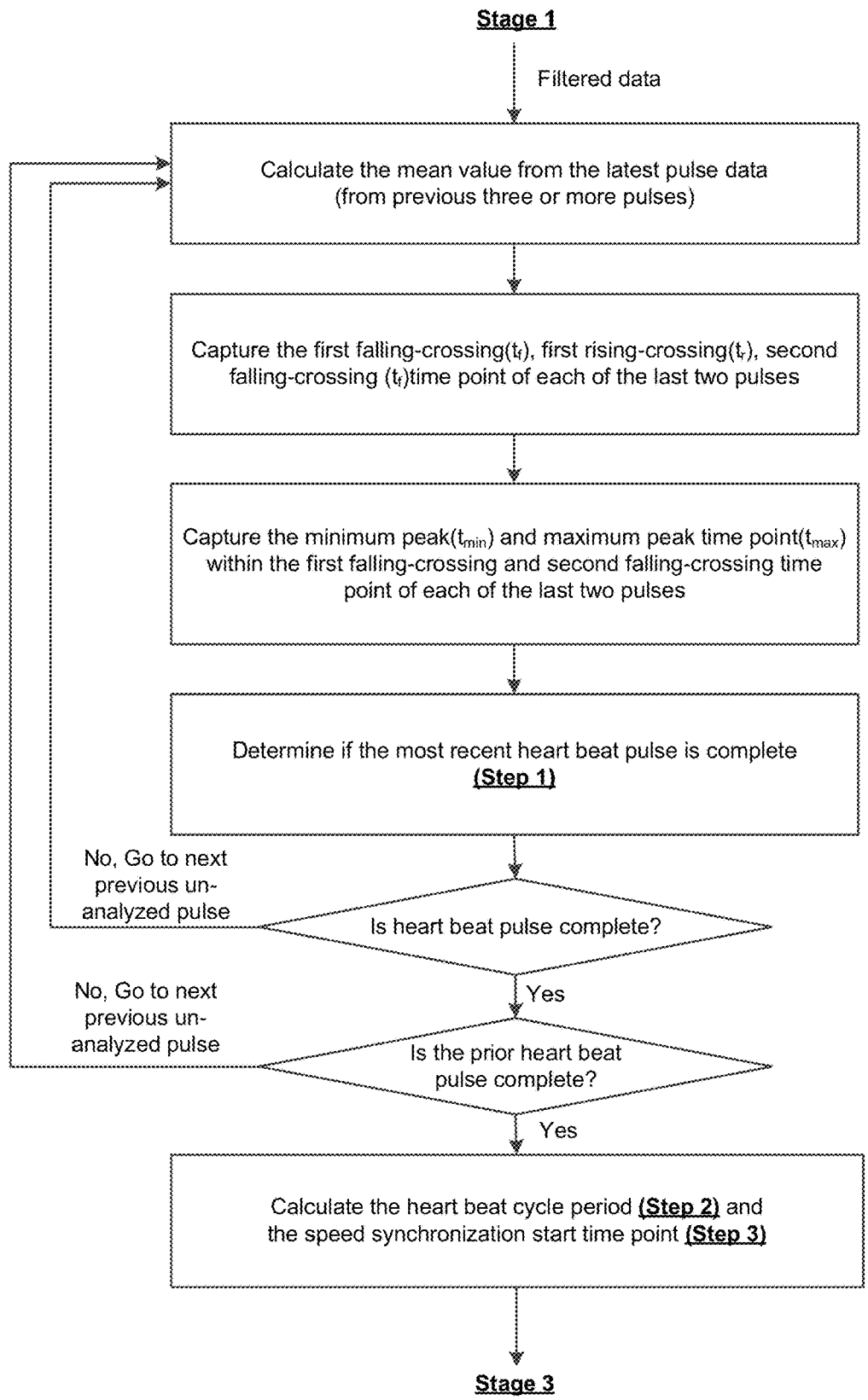
FIG. 3 shows one method of identifying a pulse period of a heart beat of one embodiment of the invention.
Figure 4:
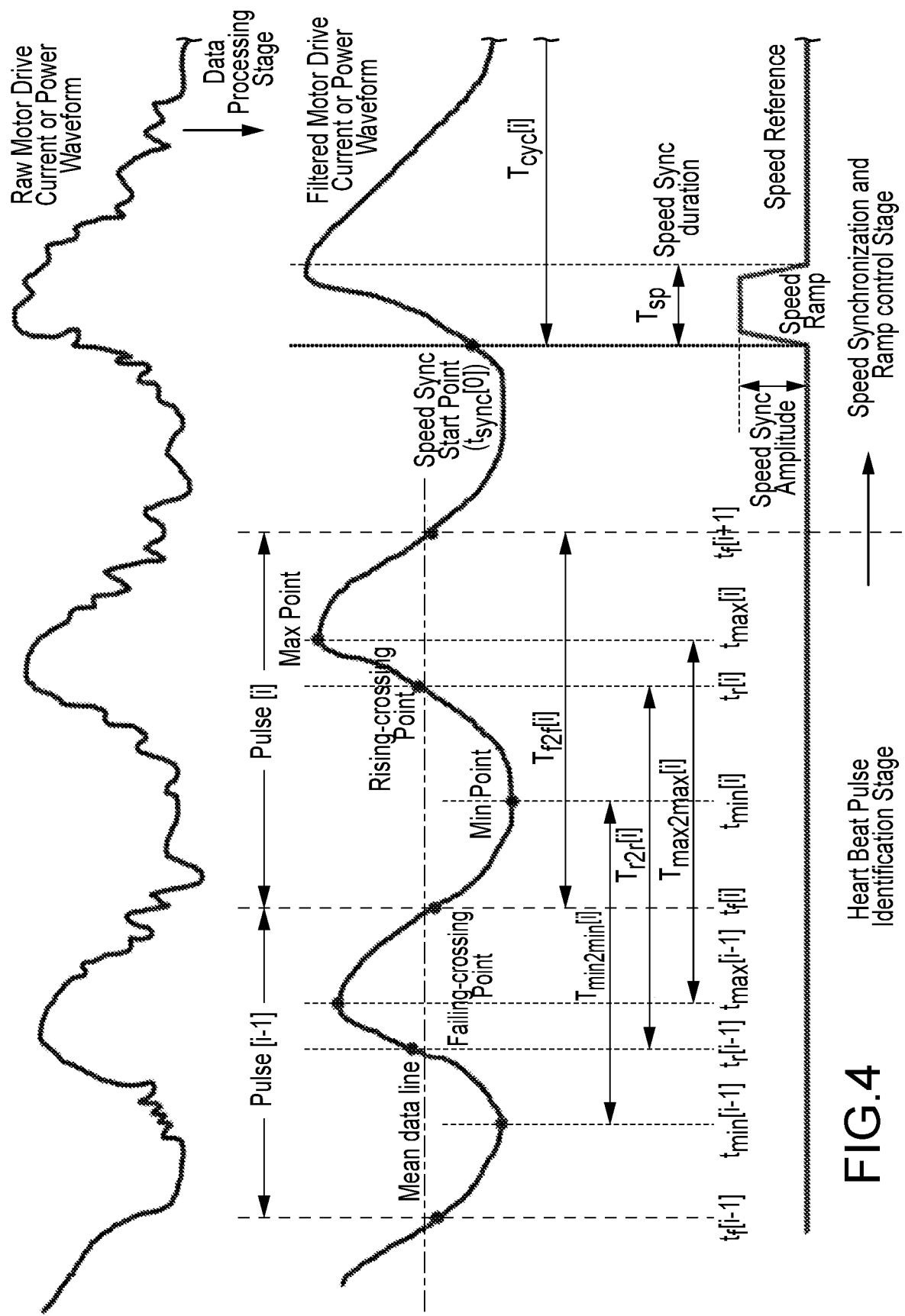
FIG. 4 motor data converted to heart beat information and various characteristics thereof pertinent to methods and system of the invention.
Figure 4:
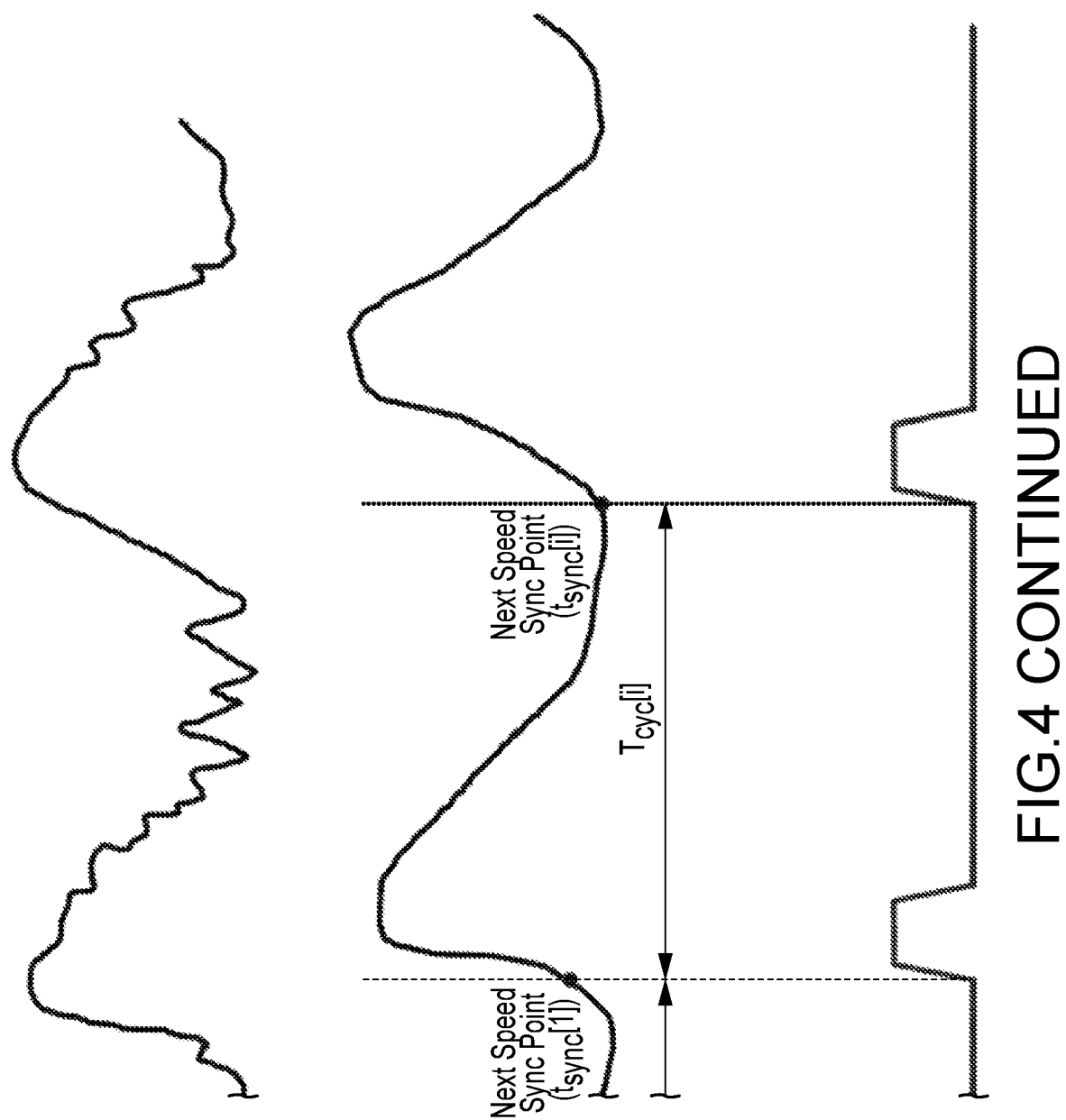

Stage 2 involves three separate steps as shown in FIG. 3:

Step 1—Determine if each pulse is complete—To determine if a pulse is complete, characteristics of the pulse may first be determined from the data provided from Stage 1. Those characteristics may include the following (see FIG. 4 for reference):

The mean amplitude value from the previous three or more pulses

The maximum amplitude value from the pulse to be analyzed

The minimum amplitude value from the pulse to be analyzed

The first falling-crossing time ($t_f$) which is the point at which the pulse first crosses the mean value on the downslope The first rising-crossing time ($t_r$) which is the point at which the pulse crosses the mean value on the upslope The second falling-crossing time ($t_f$) which is the point at which the pulse crosses the mean value on the downslope for a second time The minimum peak time point ($t_{min}$) for the minimum amplitude value The maximum peak time point ($t_{max}$) for the maximum amplitude value The following rules are then used to determine if two consecutive prior pulses are complete pulses. Both rules must be satisfied to allow the two pulses to be used as a reference for Step 2 of the process which determines the heart beat cycle period.

Rule 1: The amplitude difference between the maximum amplitude and the mean amplitude must satisfy the following:

$$c_1 \text{Diff}_{max2Min}[i] < \text{Diff}_{max2Mean}[i] < c_2 \text{Diff}_{max2Min}[i]$$

Where, $\text{Diff}_{max2Mean}[i]$=the difference between maximum amplitude and mean data at pulse[i];

$\text{Diff}_{max2Min}[i]$=the difference between maximum and minimum amplitude at pulse[i]; and $c_1$, $c_2$ are two constant coefficients.

In one embodiment $c_1$=0.375 and $c_2$=0.75, though in other embodiments other values of $c_1$ and $c_2$ may be possible.

Rule 2: The four pulse periods from different time points must satisfy the following:

$$T_{cyc\_min} < \{T_{f2f}[i], T_{r2r}[i] T_{min2min}[i], T_{max2max}[i]\} < T_{cyc\_max}$$

Where, $T_{f2f}[i]$=A pulse period from the last falling-crossing time point to current falling-crossing time point;

$T_{r2r}[i]$=A pulse period from the last rising-crossing time point to current rising-crossing time point;

$T_{min2min}[i]$=A pulse period from the last minimum time point to current minimum time point;

$T_{max2max}[i]$=A pulse period from the last maximum time point to current maximum time point; and $T_{cyc\_min}$, $T_{cyc\_max}$ are the limitations of a pulse period of heart beat.

In one embodiment $T_{cyc\_min}$=0.3 seconds (200 beats/min), $T_{cyc\_max}$=1.25 seconds (48 beats/min), though in other embodiments other values of $T_{cyc\_min}$ and $T_{cyc\_max}$ may be possible.

If these rules are not satisfied for two prior consecutive pulses, then such pulses are not adjudged to be complete pulses and pulses prior to the non-complete pulses are then analyzed until two prior consecutive complete pulse are located. Step 2 is then commenced based on such pulses.

Step 2—Determine the pulse period—To determine the pulse period the median value of the previously discussed four pulse periods is determined per the below:

$$T_{cyc}[i]=\text{Median}\{T_{f2f}[i], T_{r2r}[i], T_{min2min}[i], T_{max2max}[i]\}$$

Step 3—Calculate initial speed synchronization start point—There are at least four possible ways to determine an initial speed synchronization start point ($t_{sync}[0]$) as shown in the tables in FIGS. 6A and 6B. In the case where two conditions of different cases in the tables are indicated as being equally applicable (for example, under Case 1 and Case 2, the difference between $T_{max2max}[i]$ and $T_{cyc}[i]$ is equal to the difference between $T_{min2min}[i]$ and $T_{cyc}[i]$), the lower number Case has priority and is employed (in the example, Case 1, instead of Case 2).

After completion of Step 2 and Step 3, the process continues to Stage 3, where based on the speed synchronization start point identified in Stage 2, a pump motor is controlled to synchronize speed increases thereof with heart beats. Considering all the timing offsets such as the data filter timing delay, the phase shift between left ventricle pressure and pumping flow and motor drive current or power, pump speed ramp up and down time, all the next series of speed synchronization time points can be finalized as:

$$t_{sync}[i]=t_{sync}[0]-T_{offset}+(j-1)*T_{cyc}[i]$$

Where $T_{offset} < T_{min2max}$ and in one possible embodiment $T_{offset} \approx T_{offset} \approx 40\sim80$ ms, and J is equal to the sequential heart beat to be synchronized (i.e., J=1 at the first heart beat, J=2 at the second heart beat, etc.).

This synchronized heart beat count (J) should not be too large, since the speed synchronization at one round may rely on the results of Stages 1 and 2, which may not be matched with the current heart beat features at after some while probably due to the patient's physiology or other factors, and thus possibly cause asynchrony between the pump and heartbeat. Therefore, to get the precise real-time synchronization, it may be necessary to identify the latest heart beat cycle features and start the synchronization again after several synchronized heart beat counts. Thus $J_{max}$ may equal 10, 9, 8, 7, or fewer beats in some embodiments, though in other embodiments may exceed 10, prior to Stages 1-3 being re-initiated to ensure asynchrony between the pump and heartbeat does not occur.

Figure 5:
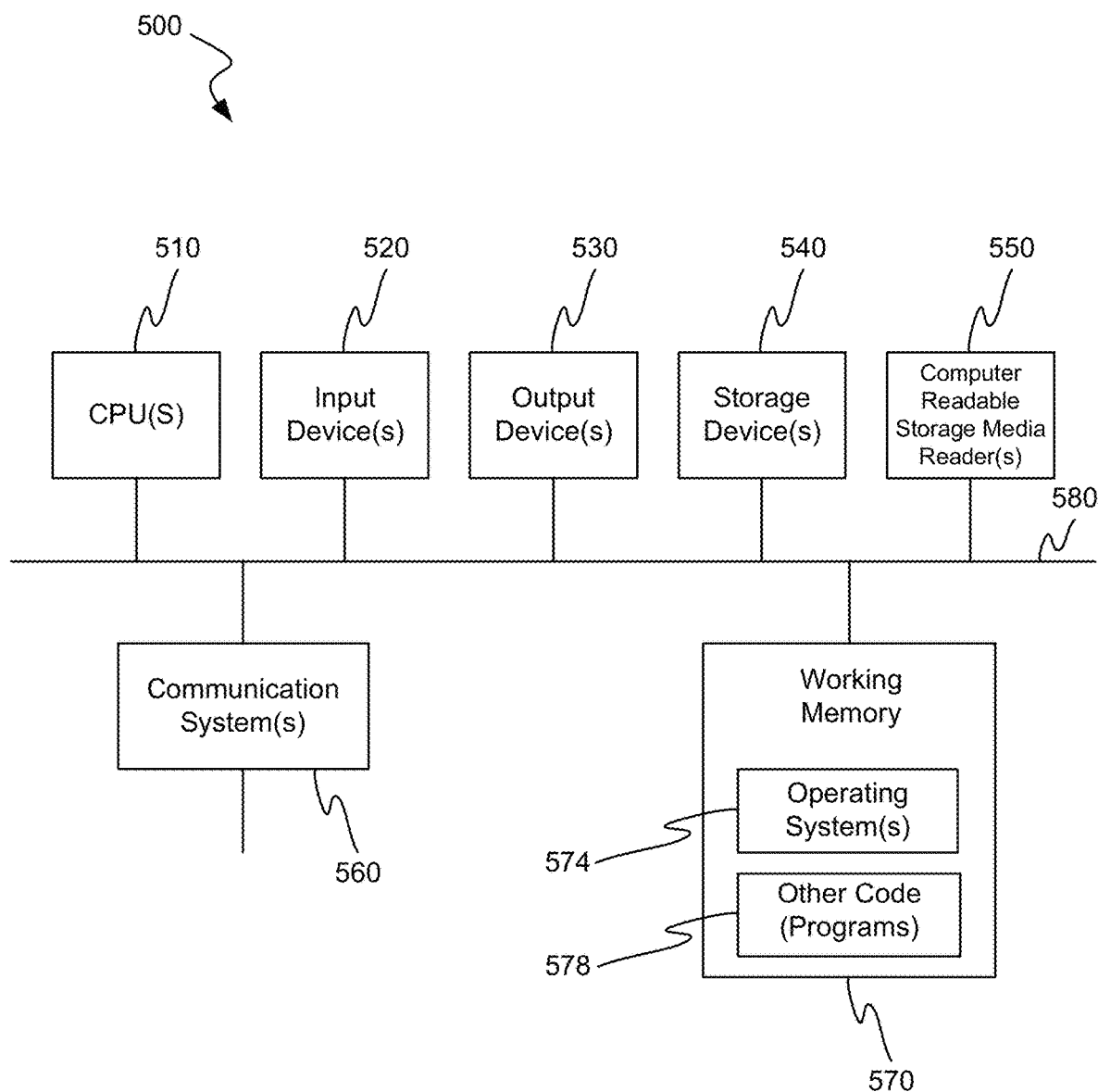
FIG. 5 is a block diagram of an exemplary computer system capable of being used in at least some portion of the apparatuses or systems of the present invention, or implementing at least some portion of the methods of the present invention.

FIG. 5 is a block diagram illustrating an exemplary processing or computer system 500 in which embodiments of the present invention may be implemented. This example illustrates a processing or computer system 500 such as may be used, in whole, in part, or with various modifications, to provide the functions of a processor controlling and receiving data back from an LVAD or other device, and/or other components of the invention such as those discussed above. For example, various functions of such processor may be controlled by the computer system 500, including, merely by way of example, receiving current or power data back from the pump motor, data processing with regard to previous heart pulses, and speed synchronization of the pump based on such data, etc.

The computer system 500 is shown comprising hardware elements that may be electrically coupled via a bus 590. The hardware elements may include one or more central processing units 510, one or more input devices 520 (e.g., data acquisition subsystems), and one or more output devices 530

(e.g., control subsystems). The computer system 500 may also include one or more storage device 540. By way of example, storage device(s) 540 may be solid-state storage device such as a random access memory ("RAM") and/or a read-only memory ("ROM"), which can be programmable, flash-updateable and/or the like.

The computer system 500 may additionally include a computer-readable storage media reader 550, a communications system 560 (e.g., a network device (wireless or wired), a Bluetooth™ device, cellular communication device, etc.), and working memory 580, which may include RAM and ROM devices as described above. In some embodiments, the computer system 500 may also include a processing acceleration unit 570, which can include a digital signal processor, a special-purpose processor and/or the like.

The computer-readable storage media reader 550 can further be connected to a computer-readable storage medium, together (and, optionally, in combination with storage device(s) 540) comprehensively representing remote, local, fixed, and/or removable storage devices plus storage media for temporarily and/or more permanently containing computer-readable information. The communications system 560 may permit data to be exchanged with a network, system, computer and/or other component described above.

The computer system 500 may also comprise software elements, shown as being currently located within a working memory 580, including an operating system 584 and/or other code 588. It should be appreciated that alternate embodiments of a computer system 500 may have numerous variations from that described above. For example, customized hardware might also be used and/or particular elements might be implemented in hardware, software (including portable software, such as applets), or both. Furthermore, connection to other computing devices such as network input/output and data acquisition devices may also occur.

Software of computer system 500 may include code 588 for implementing any or all of the function of the various elements of the architecture as described herein. Methods implementable by software on some of these components have been discussed above in more detail.

The invention has now been described in detail for the purposes of clarity and understanding. However, it will be appreciated that certain changes and modifications may be practiced within the scope of the disclosure.

The invention claimed is:

1. A method comprising:
   receiving a signal from a motor of a heart assist pump device;
   identifying two prior pulses based on the signal;
   determining that the two prior pulses are not complete;
   identifying an additional two prior pulses based on the signal;
   determining that the additional two prior pulses are complete;
   determining a pulse period based on the additional two prior pulses;
   determining a speed synchronization start point at which time the motor will begin a change in speed of operation based on the pulse period; and
   beginning the change in speed of the motor to a target speed at the speed synchronization start point.

2. The method of claim 1, wherein the signal comprises: a current signal or a power signal.

3. The method of claim 1, further comprising: filtering the signal.

4. The method of claim 3, wherein:
   filtering the signal comprises one or more employing a second order impulse response filter, an infinite impulse response filter, or a finite impulse response filter.

5. The method of claim 3, wherein:
   filtering the signal comprises filtering out a portion of the signal comprising high frequency noise data that is out of a general heart beat range.

6. The method of claim 5, wherein:
   the general heart beat range comprises a frequency of less than 5 Hz.

7. The method of claim 1, wherein:
   the pulse period comprises a median of $T_{f2f}[i]$, $T_{r2r}[i]$, $T_{min2min}[i]$ and $T_{max2max}[i]$.

8. A heart assist pump device, comprising:
   a motor; and
   a controller, wherein the controller is configured to:
   receive a signal from the motor;
   identify two prior pulses based on the signal;
   determine that the two prior pulses are not complete;
   identify an additional two prior pulses based on the signal;
   determine that the additional two prior pulses are complete;
   determine a pulse period based on the additional two prior pulses;
   determine a speed synchronization start point at which time the motor will begin a change in speed of operation based on the pulse period; and
   begin the change in speed of the motor to a target speed at the speed synchronization start point.

9. The heart assist pump device of claim 8, wherein:
   determining the speed synchronization start point comprises one or more of:
   using a maximum amplitude time point as a reference when $T_{max2max}[i]$ is most close to $T_{cyc}[i]$ such that the speed synchronization start point is equal to $t_{max}[i]+T_{cyc}[i]-T_{sp}$, where $T_{sp}$ is a duration of the increase in speed of operation;
   using a minimum amplitude time point as the reference when $T_{min2min}[i]$ is most close to $T_{cyc}[i]$ such that the speed synchronization start point is equal to $t_{min}[i]+T_{cyc}[i] T_{k1}$, where $T_{k1}=k_1 T_{min2max}$, and $k_1 \approx 0.25$ to $0.4$, which depends on the $T_{sp}$;
   using a falling-crossing time point as the reference when $T_{f2f}[i]$ is most close to $T_{cyc}[i]$ such that the speed synchronization start point is equal to $t_f[i+1]+\tau_{f2min}+T_{k1}$, where $\tau_{f2min}$ is an average of $T_{f2min}$, and $T_{k1}=k_1 T_{min2max}$; or
   using a rising-crossing time point as the reference when $T_{r2r}[i]$ is most close to $T_{cyc}[i]$ such that the speed synchronization start point is equal to $t_r[i]+T_{cyc}[i]-T_{k2}$ where $T_{k2}=k_2 T_{min2max}$, and $k_2 \approx 0.125$ to $0.3$, which depends on the $T_{sp}$.

10. The heart assist pump device of claim 8, wherein the controller is further configured to:
    increase the speed of operation of the heart assist pump device at additional speed synchronization start points as determined by $t_{sync}[j]=t_{sync}[0]-T_{offset}+(j-1)*T_{cyc}[i]$, where $T_{offset}<T_{min2max}$ and $T_{offset}\approx 40\sim 80$ ms.

11. The heart assist pump device of claim 8, wherein:
    determining that the additional two prior pulses are complete is based on at least one selection from a group consisting of:
    a mean amplitude of three or more previous pulses;
    a maximum amplitude of each pulse;
    a minimum amplitude of each pulse;

a first falling-crossing time of each pulse;
a first rising-crossing time of each pulse;
a second falling-crossing time of each pulse;
a minimum peak time point for the minimum amplitude value of each pulse; and
a maximum peak time point for the maximum amplitude value of each pulse.

12. The heart assist pump device of claim 8, wherein:
beginning the change in speed of the motor comprises increasing the speed of the motor corresponding to an increase in a rate of a cardiac cycle of a patient.

13. The heart assist pump device of claim 8, wherein:
determining that the additional two prior pulses are complete comprises:
determining that $\text{Diff}_{max2Mean}[i]$ is (1) greater than a first product of $c_1$ and $\text{Diff}_{max2Min}[i]$, and (2) is lesser than a second product of $c_2$ and $\text{Diff}_{max2Min}[i]$; and
determining that four pulse periods comprising $T_{f2f}[i]$, $T_{r2r}[i]$, $T_{min2min}[i]$; and $T_{max2max}[i]$ are each (1) greater than $T_{cyc\_min}$, and (2) less than $T_{cyc\_max}$.

14. The heart assist pump device of claim 8, wherein:
the motor is configured to operate using one or more of a set current, a set motor speed, or a set flow rate.

15. A non-transitory machine readable medium having instructions stored thereon, wherein the instructions are executable by one or more processors to at least:
receive a signal from a motor of a heart assist pump device;
identify two prior pulses based on the signal;
determine that the two prior pulses are not complete;
identify an additional two prior pulses based on the signal;
determine that the additional two prior pulses are complete;
determine a pulse period based on the additional two prior pulses;
determine a speed synchronization start point at which time the motor will begin a change in speed of operation based on the pulse period; and
begin the change in speed of the motor to a target speed at the speed synchronization start point.

16. The non-transitory machine readable medium of claim 15, wherein:
beginning the change in speed of the motor comprises increasing the speed before a systolic phase.

17. The non-transitory machine readable medium of claim 15, wherein:
beginning the change in speed of the motor comprises decreasing the speed before an end of systole.

18. The non-transitory machine readable medium of claim 15, wherein:
determining the speed synchronization start point comprises one or more of:
using a maximum amplitude time point as a reference such that the speed synchronization start point is equal to $t_{max}[i]+T_{cyc}[i]-T_{sp}$, where $T_{sp}$ is a duration of the increase in speed of operation;
using a minimum amplitude time point as the reference such that the speed synchronization start point is equal to $t_{min}[i]+T_{cyc}[i]+T_{k1}$, where $T_{k1}=k_1 T_{min2max}$, and $k_1 \approx 0.25$ to 0.4, which depends on the $T_{sp}$;
using a falling-crossing time point as the reference such that the speed synchronization start point is equal to $t_f[i+1]+\tau_{f2min}+T_{k1}$, where $T_{f2min}$ is an average of $T_{f2min}$, and $T_{k1}=k_1 T_{min2max}$; or
using a rising-crossing time point as the reference such that the speed synchronization start point is equal to $t_r[i]+T_{cyc}[i]-T_{k2}$ where $T_{k2}=k_2 T_{min2max}$, and $k_2 \approx 0.125$ to 0.3, which depends on the $T_{sp}$.

19. The non-transitory machine readable medium of claim 18, wherein:
the reference comprises:
the maximum amplitude time point when $T_{max2max}[i]$ is most close to $T_{cyc}[i]$;
the minimum amplitude time point when $T_{min2min}[i]$ is most close to $T_{cyc}[i]$;
the falling-crossing time point when $T_{f2f}[i]$ is most close to $T_{cyc}[i]$; or
the rising-crossing time point when $T_{r2r}[i]$ is most close to $T_{cyc}[i]$.

20. The non-transitory machine readable medium of claim 15, wherein the instructions further cause the one or more processors to:
filtering the signal to remove a portion of the signal comprising high frequency noise data that is out of a general heart beat range.

* * * * *